United States Patent
Sakaguchi

(12) 
(10) Patent No.: US 6,322,909 B1
(45) Date of Patent: Nov. 27, 2001

(54) ORGANIC ELECTROLUMINESCENT DEVICE COMPRISING A SQUARYLIUM COMPOUND

(75) Inventor: Yoshikazu Sakaguchi, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/337,608

(22) Filed: Jun. 21, 1999

(30) Foreign Application Priority Data

Jun. 24, 1998 (JP) .................................................. 10-177510

(51) Int. Cl.[7] .................................................. H05B 33/14
(52) U.S. Cl. ........................ 428/690; 428/917; 428/704; 313/504; 313/506
(58) Field of Search .................................. 428/690, 704, 428/917; 313/504, 506

(56) References Cited

U.S. PATENT DOCUMENTS 5,525,516 * 6/1996 Krutak et al. ............................ 436/56

OTHER PUBLICATIONS

Baowen Zhang et al., "Photoluminescence and electroluminescence of squarylium cyanine dyes", Synthetic Metals, vol. 91, pp. 237–241, Dec. 1997.*

* cited by examiner

*Primary Examiner*—Marie Yamnitzky

(74) *Attorney, Agent, or Firm*—Michael Best & Friedrich LLC; J. Warren Whitesel

(57) ABSTRACT

An organic electroluminescent device comprising a pair of a cathode and an anode and therebetween, at least one organic thin-film layer containing an emitter layer, wherein said at least one organic thin-film layer contains a squarylium compound represented by the following formula (1) or (2):

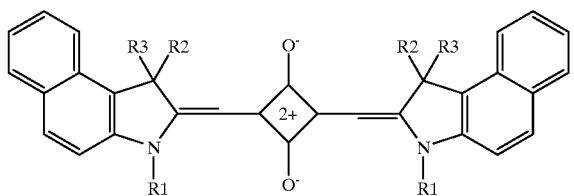

(1)

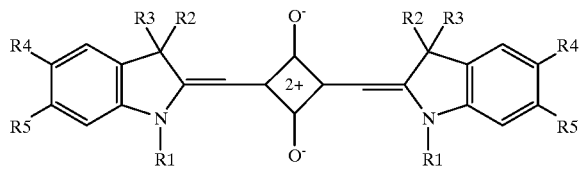

(2)

wherein R1 to R5 each independently represents a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom.

4 Claims, 2 Drawing Sheets

ORGANIC ELECTROLUMINESCENT DEVICE COMPRISING A SQUARYLIUM COMPOUND

BACKGROUND OF THE INVENTION

1. Field of the Invention

This invention relates to an organic electroluminescent device (which will hereinafter be called "organic EL device" simply) used for a planar light source or display device, particularly to a red-light emitting organic EL device.

2. Description of the Related Art

The organic EL device is considered promising as a spontaneous emission type planar display device. The organic EL device is expected to find its utility for a full color display and is therefore under brisk development, because different from an inorganic EL device which requires AC drive and high voltage, it is free from such limitations and in addition, is presumed to facilitate multi-color emission owing to a variety of usable organic compounds. When the above-described organic EL device is applied to a full color display, it is necessary for the device to emit three primary colors, that is, red, green and blue.

A number of reports have been published on green light emission and reported as a green light emitter are, for example, a device using tris(8-quinolinol)aluminum [Applied Physics Letters, 51, 913(1987)] and a device using a diarylamine derivative (Japanese Patent Application Laid-Open No.53397/1996).

There are also many reports on a blue-color emitting device, for example, a device using a stilbene compound (Japanese Patent Application Laid-Open No. 295359/1993), a device using a triarylamine derivative (Japanese Patent Application Laid-Open No. 53955/1995), a device using a tetraaryldiamine derivative (Japanese Patent Application Laid-Open No. 48656/1996) and a device using a styrylated biphenyl compound (Japanese Patent Application Laid-Open No. 132080/1994). In addition, it has been reported that a distyrylarylene derivative used as a light emitting material exhibited brightness of at least 20000 cd/m$^2$, luminous efficiency of 5 lm/W and half life of at least 5000 hours (special lecture at the 70th Spring Annual Meeting of The Chemical Society of Japan).

Concerning an organic EL device from which red light emission is available, red light emission is obtained by the conversion of the wavelength of blue light emission in a fluorescent dye layer according to Japanese Patent Application Laid-Open No. 152897/1991, while it is obtained by doping of a red fluorescent dye into an emitter layer from which green or blue light emission is available according to Japanese Patent Application Laid-Open Nos 272854/1995, 288184/1995 or 286033/1996. Neither is sufficient from the viewpoints of brightness and color purity. Japanese Patent Application Laid-Open No. 791/1991 discloses an organic EL device using a red fluorescent dye singly for an emitter layer. Although Japanese Patent Application Laid-Open No.93257/1994 discloses the use of a squarylium compound represented by the following structural formula:

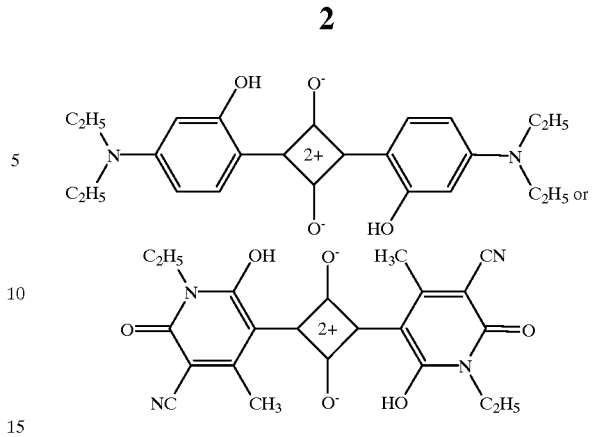

as a dopant in an emitter layer, red light emission of the resulting device is not sufficient in color purity. Further improvement is necessary for the practical use of it.

The above-described method according to the conversion of the wavelength of blue light emission in a fluorescent dye layer is also accompanied with the problems that sufficient luminous efficiency cannot be attained because a quantum yield for color conversion of EL light emission through the fluorescent dye layer is limited; and the use of the layer inevitably raises the production cost.

In addition, the red-light emitting material exemplified in the above conventional example has a low quantum yield of fluorescence and even by an increase in the electric current flowing inside of the device, light is emitted only at brightness of about 1000 cd/m$^2$ so that it is not suited for practical use.

SUMMARY OF THE INVENTION

The present invention has been completed with a view to overcoming the above-described problems and an object of the present invention is to provide a red-light emitting organic EL device having high brightness, excellent color purity and excellent luminous life.

The above-described object can be accomplished by the means which will be described below. In the present invention, there is provided an organic EL device which comprises a pair of a cathode and an anode and, therebetween, at least one organic thin-film layer containing an emitter layer, wherein (a) said at least one organic thin-film layer comprises a squarylium compound represented by the following structural formula (1):

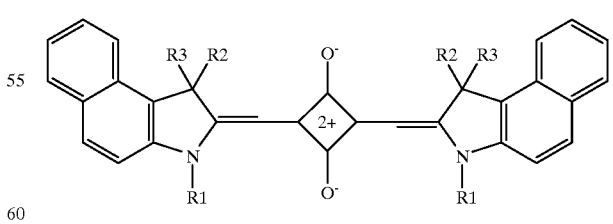

(1)

wherein R1 to R3 each independently represents a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom, or by the following structural formula (2):

(2)

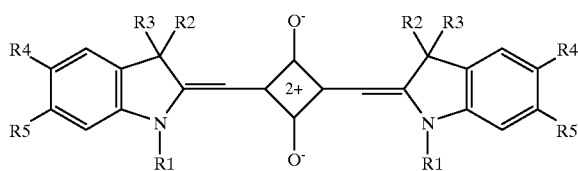

wherein R1 to R5 each independently represents a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom.

Also embraced is the above-described organic EL device wherein:

(b) said emitter layer comprises a green to yellow-light emitting material having an EL spectrum of 500 nm to 580 nm and a squarylium compound represented by the above-described structural formula (1) or (2);

(c) said emitter layer comprises a quinoline metal complex and a squarylium compound represented by the above-described structural formula (1) or (2); or (d) said squarylium compound represented by the above-described structural formula (1) or (2) is contained in an amount ranging from 0.001 to 50 wt. % based on a host material.

The red-light emitting material according to the present invention is fluorescent, having an absorption band in a green color region and a high quantum yield in a red color region of 600 to 650 nm so that red color emission inevitable for application of an organic EL device to a color display can be attained at high brightness and high efficiency.

In addition, the material according to the present invention does not disturb transfer of carriers injected into the organic EL device, because owing to a high quantum yield, even a trace amount of it mixed in the emitter layer of the organic EL device permits light emission in a red-color region at a high brightness. Furthermore, the material according to the present invention can be easily formed into a thin film by the electric resistance heating type film formation method. The thin film thus formed is markedly stable and excellent in flatness, and no change in the film structure such as crystallization or formation of a coagulated state is recognized, which facilitates extension of the life of the organic EL device.

Thus, the organic EL device using the material of the present invention is effective as a red light emitting device for a color display device.

DETAILED DESCRIPTION OF THE PREFERRED EMBODIMENTS

The present invention will hereinafter be described more specifically.

Figure 1:
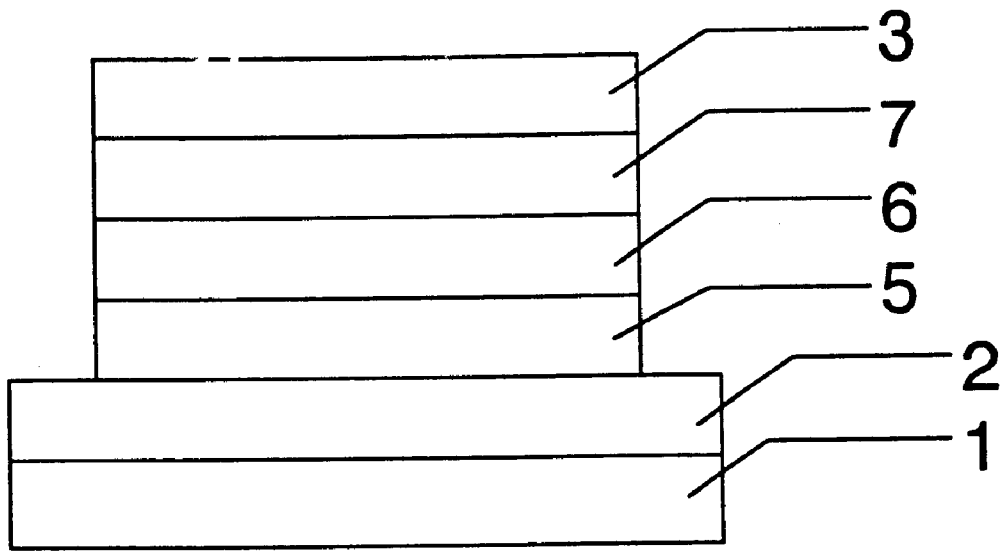
FIGS. 1 to 4 are cross-sectional views each illustrating an organic EL device relating to examples of the present invention.

FIG. 1 is a cross-sectional view illustrating one example of the organic EL device of the present invention, which is formed by successively disposing a hole transporting layer 5, an emitter layer 6 and an electron transporting layer 7 between an anode 2 disposed on a glass substrate 1 and a cathode 3.

Figure 2:
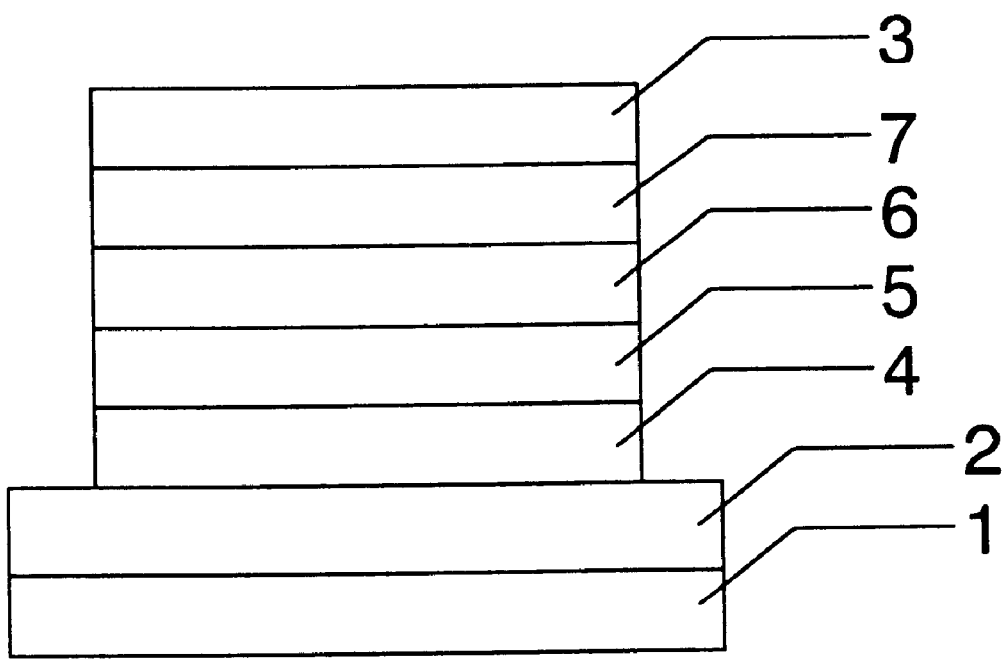
Figure 3:
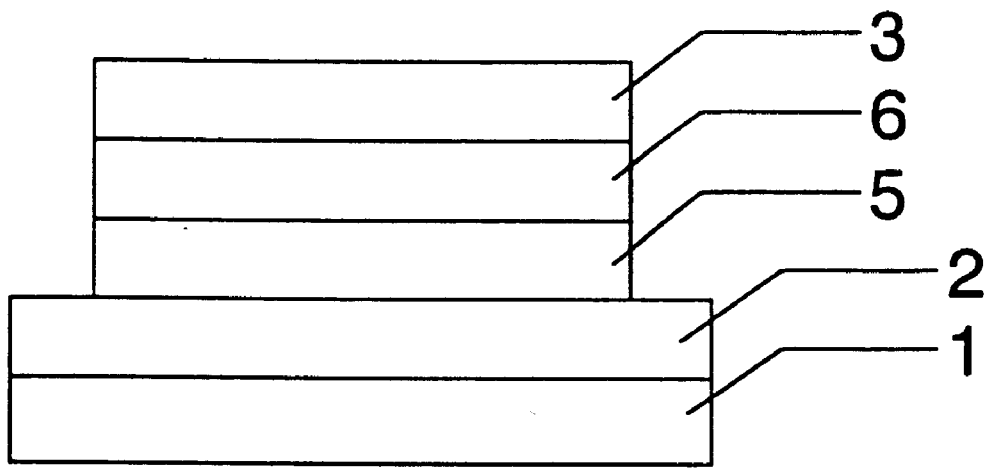
Figure 4:
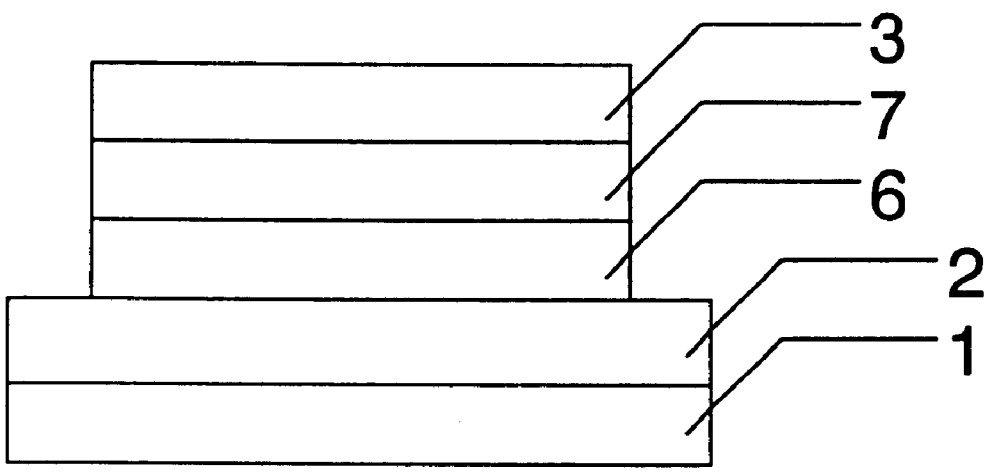

Examples of the organic EL device include, in addition to the one as illustrated in FIG. 1, the one as illustrated in FIG. 2 which is formed by successively disposing a hole injecting layer 4, a hole transporting layer 5, an emitter layer 6 and an electron transporting layer 5 between an anode 2 disposed on a glass substrate 1 and a cathode 3; the one as illustrated in FIG. 3 which is formed by disposing a hole transporting layer 5 and an emitter layer 6 between an anode 2 and a cathode 3; and the one as illustrated in FIG. 4 which is formed by disposing an emitter layer 6 and an electron transporting layer 7 between an anode 2 and a cathode 3.

The organic EL device according to the present invention is made to contain, in the emitter layer 6 of the above-described structures, a squarylium compound represented by the following structural formula (1):

(1)

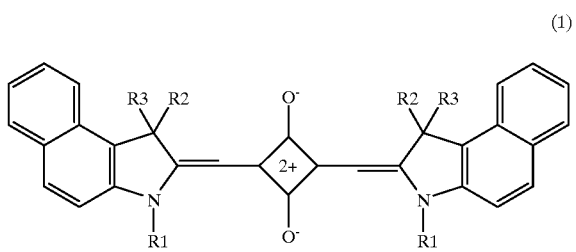

wherein R1 to R3 each independently represents a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom, or represented by the following structural formula (2):

(2)

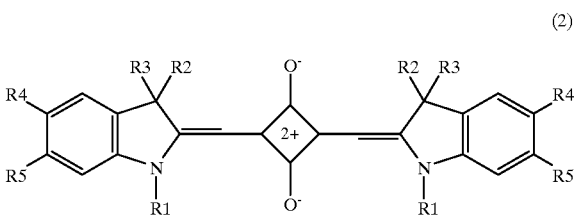

wherein R1 to R5 each independently represents a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom.

Examples of the substituted or unsubstituted alkyl group defined by R1 to R3 of formula (1) or R1 to R5 of formula (2) include methyl, ethyl, n-propyl, iso-propyl, n-butyl, sec-butyl, tert-butyl, pentyl and trichloromethyl. Examples of the substituted or unsubstituted alkoxy group defined by R1 to R3 of formula (1) or R1 to R5 of formula (2) include methoxy, ethoxy, n-butoxy, tert-butoxy, trichloromethoxy and trifluoroethoxy. Examples of the aryl group defined by R1 to R3 of formula (1) or R1 to R5 of formula (2) include phenyl and naphtyl.

Specific examples of the above-described compounds are shown in Table 1. It should however be borne in mind that the compounds are not limited thereto.

TABLE 1

| Substituent of structural formula (1) | Substituent of structural formula (2) |
|---|---|
| $R_1=R_2=R_3=CH_3$ | $R_1=R_2=R_3=CH_3$ |
|  | $R_4=R_5=H$ |
| $R_1=C_2H_5$ | $R_1=R_2=R_3=R_5=CH_3$ |
| $R_2=R_3=CH_3$ | $R_4=H$ |
| $R_1=C_3H_7$ | $R_1=C_2H_5$ |
| $R_2=R_3=CH_3$ | $R_2=R_3=CH_3$ |
|  | $R_4=R_5=H$ |
| $R_1=C_5H_{11}$ | $R_1=C_4H_9$ |
| $R_2=R_3=CH_3$ | $R_2=R_3=CH_3$ |
|  | $R_4=R_5=H$ |
| $R_1=C_2H_5$ | $R_1=C_6H_5$ |
| $R_2=R_3=H$ | $R_2=R_3=CH_3$ |
|  | $R_4=R_5=H$ |
| $R_1=OCH_3$ | $R_1=C_2H_5$ |
| $R_2=R_3=CH_3$ | $R_2=R_3=CH_3$ |
|  | $R_4=H$ |
|  | $R_5=OCH_3$ |
| $R_1=C_6H_5$ | $R_1=C_2H_5$ |
| $R_2=R_3=H$ | $R_2=R_3=CH_3$ |
|  | $R_4=H$ |
|  | $R_5=OH$ |
|  | $R_1=R_2=R_3=CH_3$ |
|  | $R_4=H$ |
|  | $R_5=Cl$ |

Among the compounds shown in Table 1, 2,4-bis-[(1,3,3-trimethyl-2-benzoindolinylidene)methyl]-squarylium of the following structural formula:

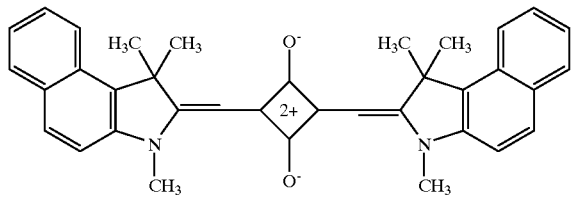

and 2,4-bis[(1-ethyl-3,3-dimethyl-2-indolinylidene)-methyl]-squarylium represented by the following structural formula:

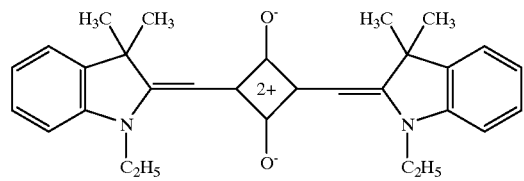

are particular preferred in consideration of brightness, luminous efficiency, brightness half-life and chromaticity coordinate.

The squarylium compound used in the present invention can be obtained by condensation reaction of squarylic acid, i.e., 3,4-dihydroxy-3-cyclobutene-1,2-dion, with a compound having a corresponding chromophore. In the condensation reaction, it is preferably to use a solvent. Examples of the solvent include alcohol such as methylalcohol, ethylalcohol, 1-propylalcohol, 2-propylalcohol, 1-butylalcohol and 2-butylalcohol; and a mixed solvent of said alcohol and aromatic hydrocarbon such as benzene, toluene and xylene. The reaction temperature is preferably in the range of 70 to 120° C. For example, a squarylium compound wherein each of R1, R2 and R3 is $CH_3$ and R4 and R5 are hydrogen in formula (2) is obtained by the following procedures: Firstly, 3,4-dihydroxy-3-cyclobutene-1,2-dion is dissolved in 1-propylalcohol and then the resultant solution is heated to about 100° C. (1,3,3-trimethyl-2-indolinylidene)methyl and toluene are added to the heated solution. After the completion of the reaction, the reaction mixture is cooled and then purified by column chromatography to obtain.

Examples of the host material for the emitter layer include 8-hydroxyquinoline metal complexes typified by tris(8-quinolinol)aluminum of the following structural formula:

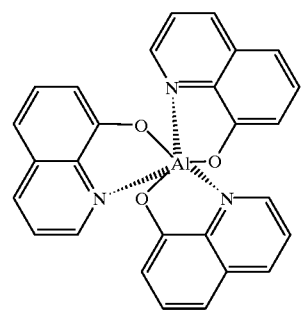

distyrylbenzene derivatives such as 1,4-bis(2-methylstyryl)benzene, bisstyrylanthracene derivatives, coumarin derivatives, oxathiazole derivatives and perinone derivatives. Particularly, 8-hydroxyquinoline metal complexes typified by tris(8-quinolinol)aluminum, coumarin derivatives and the like are preferably used in combination with the above exemplified squarylium compounds, because they bring about high brightness and luminous efficiency.

It is also possible to employ, for the emitter layer, a mixture of the above-described squarylium compound as a light emitting material with a hole transporting material or electron transporting material.

It is necessary to mix the above-described squarylium compound in an amount of 0.001 to 50 wt. % relative to the host material of the emitter layer. Amounts of the squarylium compound less than 0.001 wt. % deteriorate chromaticity, while those exceeding 50 wt. % cause concentration quenching or reduction in luminous efficiency. Amounts outside the above range are therefore not preferred.

The emitter layer is preferred to have a thickness falling within a range of 10 to 100 nm.

Although no particular limitation is imposed on a hole injecting material for forming the hole injecting layer 4 of the organic EL device of the present invention, a metallophthalocyanine or metal-free phthalocyanine represented by the following structural formula:

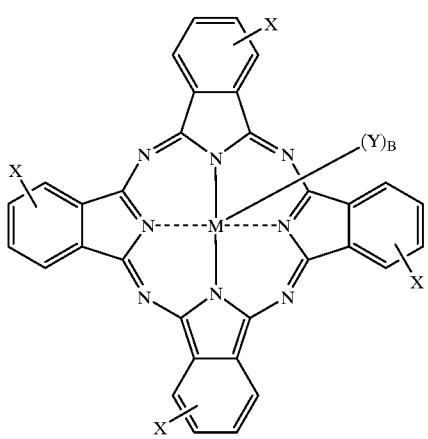

wherein X represents a hydrogen atom and M-Y is selected from Cu, VO, TiO, Mg and H$_2$, and starburst type molecules represented by the following structural formula:

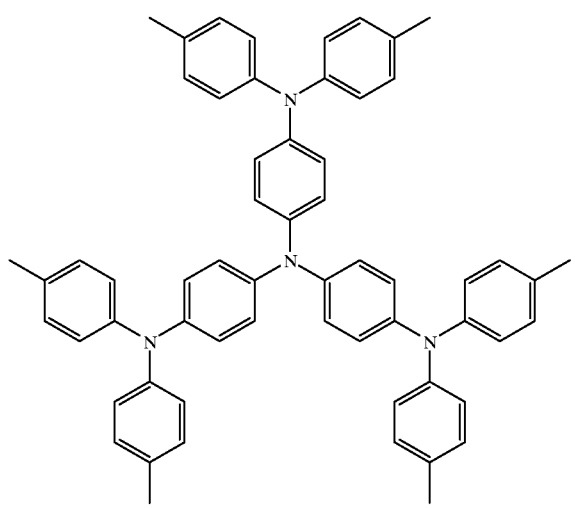

such as 4,4',4"-tris(di-p-methylphenylamino) triphenylamine can be used.

There is no particular limitation imposed on the hole transporting material used for the formation of the hole transporting layer of the organic EL device of the present invention insofar as it is a compound ordinarily used as a hole transporting material. Examples include starburst type molecules such as bis(di(p-tolyl)aminophenyl)-1,1-cyclohexane represented by the following structural formula:

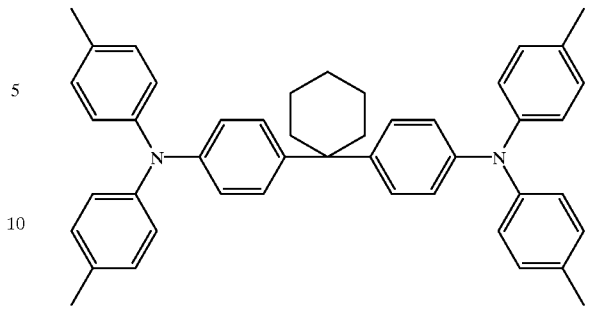

N,N'-diphenyl-N,N'-bis(3-methylphenyl)-1,1'-biphenyl-4,14-diamine represented by the following structural formula:

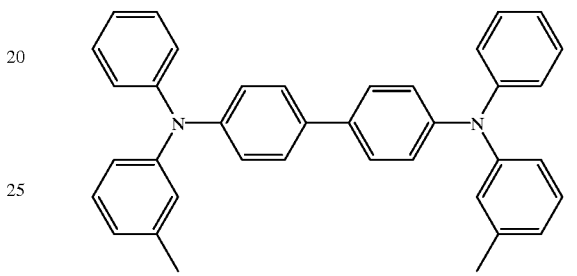

N,N'-diphenyl-N-N-bis(1-naphthyl)-(1,1'-biphenyl)-4,4'-diamine represented by the following structural formula:

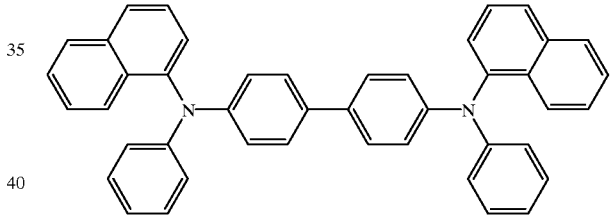

and compounds represented by the following structural formula:

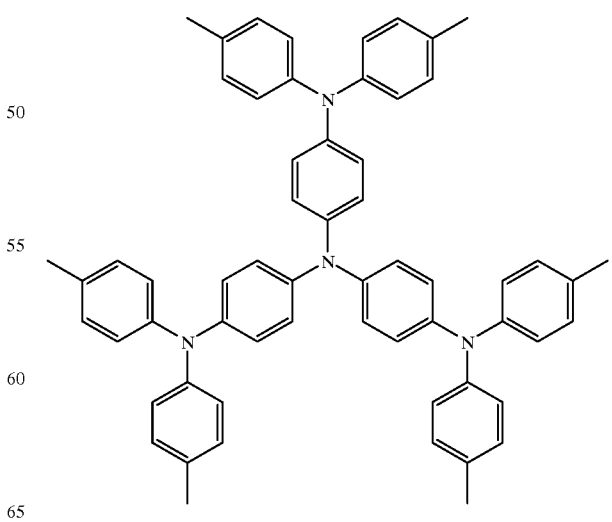

There is no particular limitation imposed on the electron transporting material used for the formation of the electron transporting layer of the organic EL device of the present invention insofar as it is a compound ordinarily employed as an electron transporting material.

Examples include oxadiazole derivatives such as 2-(4-biphenyl)-5-(4-t-butylphenyl)-1,3,4-oxadiazole represented by the following structural formula:

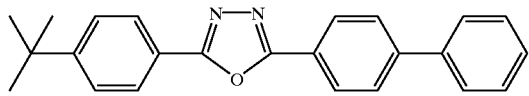

and bis{2-(4-t-butylphenyl)-1,3,4-oxadiazole}-m-phenylene represented by the following structural formula:

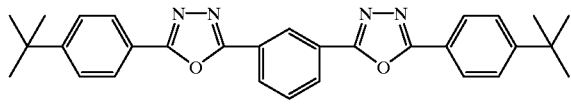

triazole derivatives, oxine metal complexes, pyrazine derivatives, pyridine derivatives, perylene derivatives, perinone derivatives and bisstyryl derivatives.

For the anode, a material which is transparent and has a large work function is employed. Examples include conductive metal oxides such as indium tin oxide (ITO), tin oxide and indium oxide, gold, platinum, and chromium. As a material for the cathode, on the other hand, a metal having a small work function is employed. In addition, alloys of such a metal with an alkali metal or alkaline earth metal is also employed. For example, aluminum, silver or tin and the alloys thereof with lithium, magnesium, potassium or sodium can be mentioned by way of example.

When the squarylium derivative and another material are subjected to co-deposition upon formation of the emitter layer, care must be exercised to the doping concentration and position.

The present invention will hereinafter be described more specifically by examples.

EXAMPLE 1

A cross-sectional structure of the organic EL device relating to Example I is shown in FIG. 1. The organic EL device of this example is composed of a transparent supporting substrate (glass substrate) 1, an anode 2 formed on glass substrate 1 and a cathode 3, and organic thin-film layers 5 to 7 sandwiched between anode 2 and cathode 3. The fabrication procedure of the organic EL device according to Example 1 will next be described. First, ITO was sputtered on glass substrate 1 to form a film having a sheet resistance of 15 Ω/□ as anode 2. The glass substrate having ITO formed thereon was subjected to ultrasonic washing with pure water and isopropyl alcohol, respectively, followed by drying over boiled isopropyl alcohol. The resulting substrate was washed further in an UV ozone washer and attached to a substrate holder of a vacuum deposition chamber.

In molybdenum-made boards, 200 mg of N,N'-diphenyl-N,N'-bis(α-naphthyl)-1,1'-biphenyl-4,4'-diamine (which will hereinafter be abbreviated as "α-NPD") as a hole transporting layer 5, 200 mg of tris(8-quinolinol)aluminum (which will hereinafter be abbreviated as "Alq3") as a host of the emitter layer 6 and an electron transport layer 7 and 100 mg of 2,4-bis[(1,3,3-trimethyl-2-benzoindolinylidene) methyl]-squarylium as a guest of the emitter layer were charged, respectively. After the resulting boards were each attached to a current-carrying terminal, the vacuum chamber was evacuated to $2 \times 10^{-4}$ Pa. The board containing α-NPD therein was energized and deposition was effected at a deposition rate of 0.3 nm/sec until the film thickness reached 50 nm. Then, the boards containing therein tris(8-quinolinol) aluminum and 2,4-bis[(1,3,3-trimethyl-2-benzoindolinylidene)methyl]-squarylium were energized so that the deposition rate of the former would be 0.3 nm/sec and that of the latter would be 0.03 nm/sec by using respective deposition power supplies. After the deposition rate of each of the materials became stable, a shutter was opened. When the thickness of the mixed film reached 30 nm, the deposition power source for 2,4-bis[(1,3,3-trimethyl-2-benzoindolinylidene)methyl]-squarylium was cut and deposition of only tris(8-quinolinol)aluminum was continued to give a thickness of 30 nm.

Then, a stainless-made shadow mask was installed on the upper part of the resulting device having a structure of substrate/ITO/α-NPD/tris(8-quinolinol)aluminum: 2,4-bis [(1,3,3-trimethyl-2-benzoindolinylidene)methyl]-squarylium/tris(8-quinolinol)aluminum. Aluminum (3 g) was charged in a BN-made boat, to which a current-carrying terminal was attached. Similarly, 500 mg of Li was charged in a tungsten-made filament, to which another current-carrying terminal was attached. After the vacuum chamber was evacuated to $1 \times 10^{-4}$ Pa, the boat was energized so that the deposition rate of aluminum would be 0.2 nm/Sec and at the same time, the filament was energized by another deposition power supply so that the deposition rate of lithium would be 0.02 to 0.03 nm/Sec. When the deposition rate of each of the both materials became stable, the shutter was opened. The deposition power supply for lithium was cut when the thickness of the mixed film became 20 nm. Formation of the aluminum film was continued until the film thickness reached 170 nm, whereby cathode 3 was formed. The pressure of the vacuum chamber was raised back to the atmospheric pressure and an organic EL device having a structure of supporting substrate/ITO/α-NPD/tris(8-quinolinol)aluminum: 2,4-bis[(1,3,4-trimethyl-2-benzoindolinylidene)methyl)]-squarylium/tris(8-quinolinol) aluminum/AlLi/Al was fabricated. When a voltage of 10V was applied to the device with the ITO as a positive electrode and with the aluminum electrode as a negative electrode, the electric current was 9 mA/cm$^2$ and the maximum brightness was 5900 cd m$^2$ (24V). The chromaticity coordinates at 400 cd/m$^2$ were (X 0.641, Y 0.328), indicating red-light emission, and the luminous efficiency at that time was 0.83 lm/W (lumen/watt).

The device was subjected to a driving test at the initial brightness of 400 cd/m$^2$ in nitrogen atmosphere, resulting in the brightness half-time of 2300 hours.

As a result of observation of the non-luminous portion called "dark spot" after storage of the resulting device for 5000 hours in nitrogen atmosphere, the state of the device was similar to that just after the film formation and growth was not recognized at all.

EXAMPLE 2

A glass substrate having ITO formed thereon, which had been prepared in a similar manner to Example 1, was attached to a deposition chamber. In molybdenum-made boards, 200 mg of N,N'-diphenyl-N,N'-di(3-methylphenyl)-1,1'-biphenyl-4,4'-diamine (TPD) as a hole injecting and transporting material, 200 mg of tris(8-quinolinol)aluminum as a host and electron transporting layer and 100 mg of 2,4-bis[(1-ethyl-3,3-dimethyl-2-indolinylidene)methyl]-squarylium as a guest were charged, respectively. After the resulting boards were attached to a current-carrying terminal, the vacuum chamber was evacuated to $2\times10^{-4}$ Pa. The board containing therein the hole injecting and transporting material was energized and deposition was effected at a deposition rate of 0.3 nm/Sec until the film thickness reached 50 nm. Then, the boards containing therein tris(8-quinolinol)aluminum and 2,4-bis[(1-ethyl-3,3-dimethyl-2-indolinylidene)methyl]-squarylium were energized and co-deposition was effected at a deposition rate of 0.3 nm/Sec for the former and 0.02 to 0.03 nm/Sec for the latter until the film thickness became 30 nm. Then, only tris(8-quinolinol) aluminum was deposited to give a thickness of 30 nm.

A stainless-made shadow mask was then attached to the upper part of the resulting device having a structure of supporting substrate/ITO/TPD/tris(8-quinolinol)aluminum: 2,4-bis[(1-ethyl-3,3-dimethyl-2-indolinylidene)methyl]-squarylium/tris(8-quinolinol)aluminum. Aluminum (3 g) was charged in a BN-made boat, to which a current-carrying terminal was attached. Similarly, 500 mg of Li was charged in a tungsten-made filament, to which another current-carrying terminal was attached. After the vacuum chamber was evacuated to $1\times10^{-4}$ Pa, the boat was energized so that the deposition rate of aluminum would be 0.2 nm/Sec and at the same time, the filament was energized by another deposition power supply so that the deposition rate of lithium would be 0.02 to 0.03 nm/Sec. When the deposition rate of each of the both materials became stable, the shutter was opened. The deposition power supply for lithium was cut when the thickness of the mixed film became 20 nm. Formation of the aluminum film was continued until the film thickness reached 170 nm. The pressure of the vacuum chamber was raised back to the atmospheric pressure and an organic EL device composed of supporting substrate/ITO/TPD/tris(8-quinolinol)aluminum: 2,4-bis[(1-ethyl-3,3-dimethyl-2-indolinylidene)methyl]-squarylium/tris(8-quinolinol)aluminum/AlLi/Al was fabricated. When a voltage of 10V was applied to the device with the ITO as a positive electrode and with the aluminum electrode as a negative electrode, electric current was 8 mA/cm$^2$, the maximum brightness was 5500 cd/m$^2$ (24V) and the chromaticity coordinates at 400 cd/m$^2$ were (X 0.619, Y 0.340) indicating red light emission. The luminous efficiency at that time was 0.78 lm/W (lumen/watt).

The device was subjected to a driving test at the initial brightness of 400 cd/m$^2$ in nitrogen atmosphere, resulting in brightness half-time of 2300 hours.

As a result of observation of the non-luminous portion called "dark spot" after storage of the resulting device for 5000 hours in nitrogen atmosphere, the state of the device was similar to that just after the film formation and growth was not recognized at all.

EXAMPLE 3

A glass substrate having ITO formed thereon, which had been prepared in a similar manner to Example 1, was attached to a deposition chamber. In five crucibles made of high-purity graphite, 1 g of copper phthalocyanine as a hole injecting material, 1 g of N,N'-diphenyl-N,N'-bis(α-naphthyl)-1,1'-biphenyl-4,4'-diamine (α-NPD) as a hole transporting material, 1 g of tris(8-quinolinol)aluminum as a luminous host material, 1 g of 2,4-bis[(1,3,3-trimethyl-2-benzoindolinylidene)methyl]-squarylium as a luminous guest material and 1 g of bis{2-(4-t-butylphenyl)-1,3,4-oxadiazole}-m-phenylene as an electron transporting material were charged, respectively. The crucibles were attached to respective current-carrying terminals.

The vacuum chamber was evacuated to $1\times10^{-4}$ Pa. The crucible containing therein copper phthalocyanine was energized and a film was formed at a deposition rate of 0.3 nm/Sec until the film thickness reached 30 nm. The crucible charged with α-NPD was energized and a film was formed at a deposition rate of 0.3 nm/Sec to give a film thickness of 30 nm. Then, the crucibles charged with tris(8-quinolinol) aluminum and 2,4-bis[(1,3,3-trimethyl-2-indolinylidene) methyl]-squarylium were energized, respectively. Electric currents were controlled so that the deposition rate of tris(8-quinolinol)aluminum would be 0.3 nm, while that of 2,4-bis[(1,3,3-trimethyl-2-indolinylidene)methyl]-squarylium would be 0.02 to 0.03 nm/Sec and when both became stable, co-deposition was initiated simultaneously. When the film thickness became 20 nm as tris(8-quinolinol) aluminum, power supply for 2,4-bis[(1,3,3-trimethyl-2-indolinylidene)methyl]-squarylium was cut. Deposition of tris(8-quinolinol)aluminum was still continued to give a film thickness of 20 nm.

The crucible charged with bis{2-(4-t-butylphenyl)-1,3,4-oxadiazole}-m-phenylene was energized and film formation was conducted at a deposition rate of 0.4 nm/Sec to give a film thickness of 30 nm.

On the resulting device having a structure of supporting substrate/ITO/copper phthalocyanine/α-NPD/tris(8-quinolinol)aluminum: 2,4-bis[(1,3,3-trimethyl-2-benzoindolinilidene)methyl)]-squarylium/tris(8-quinolinol) aluminum/bis{2-(4-t-butylphenyl)-1,3,4-oxadiazole}-m-phenylene, a cathode was formed in a similar manner to Example 1. As a result of a continuity test in a similar manner to Example 1, electric current was 8 mA/cm$^2$ and the maximum brightness was 5300 cd/m$^2$ (24V) when the voltage applied was 10V. The chromaticity coordinates at 400 cd/m$^2$ were (X 0.630, Y 0.347) indicating red light emission and the luminous efficiency at that time was 0.80 lm/W.

The device was subjected to a driving test at the initial brightness of 400 cd/m$^2$ in nitrogen atmosphere, resulting in brightness half-time of 2900 hours.

As a result of observation of the non-luminous portion called "dark spot" after storage of the resulting device for 5000 hours in nitrogen atmosphere, the state of the device was similar to that just after the film formation and growth was not recognized.

EXAMPLE 4

In a similar manner to Example 3 except for the use of 2,4-bis[(1-ethyl-3,3-dimethyl-2-indolinylidene)methyl]-squarylium as an emitter guest material, an organic EL device was fabricated. When the device was subjected to a continuity test at 10V, electric current corresponding to an electric density of 8 mA/cm$^2$ flew through the device and red light emission having the maximum brightness of about 5000 cd/m$^2$ and the chromaticity coordinates of (X 0.610, Y 0.345) at 400 cd/m$^2$ was obtained.

EXAMPLE 5

After a glass substrate having ITO formed thereon, which had been prepared as in Example 1, was attached to a deposition chamber, 1 g of bis(di(p-tolyl)aminophenyl)-1,1-cyclohexane was charged as a hole transporting material in a crucible made of high-purity graphite, while 1 g of 2,4-bis[(1,3,3-trimethyl-2-benzoindolinylidene)methyl]-squarylium was charged as an emitter material in another crucible. The vacuum chamber was evacuated to $1\times10^{-4}$ Pa. The crucible charged with bis(di(p-tolyl)aminophenyl)-1,1-cyclohexane was then energized and film formation was carried out at a deposition rate of 0.3 nm/Sec until the film thickness became 50 nm. The crucible charged with 2,4-bis[(1,3,3-trimethyl-2-benzoindolinylidene)methyl]-squarylium was then energized and film formation was carried out at a deposition rate of 0.2 nm/Sec until the film thickness became 25 nm. On the resulting device having a structure of supporting substrate/ITO/bis(di(p(tolyl)aminophenyl)-1,1-cyclohexane/2,4-bis[(1,3,3-trimethyl-2-benzoindolinylidene)methyl]-squarylium, a cathode was formed in a similar manner to Example 1. After the EL device was taken out from the deposition chamber, a continuity test was conducted as in Example 1. Consequently, by the application of voltage at 20V, an electric current of 5.0 mA/cm$^2$ flew through the device and red light emission having brightness of 390 cd/m$^2$ was obtained.

EXAMPLE 6

In a similar manner to Example 5 except for the use of 2,4-bis[(1-ethyl-3,3-dimethyl- 2-indolinylidene)methyl]-squarylium as an emitter material, an organic EL device was fabricated. The device was subjected to a continuity test as in Example 5. By the application of 20V, an electric current corresponding to electric density of 4.6 mA/cm$^2$ flew through the device and red light emission having brightness of 350 cd/m$^2$ was obtained.

EXAMPLE 7

After a glass substrate having ITO formed thereon, which had been prepared as in Example 1, was attached to a deposition chamber, 1 g of bis{2-(4-t-butylphenyl)-1,3,4-oxadiazole}-m-phenylene was charged as an electron transporting material in a crucible made of high-purity graphite, while 1 g of 2,4-bis[(1,3,3-trimethyl-2-benzoindolinylidene)methyl]-squarylium was charged as an emitter material in another crucible. The vacuum chamber was evacuated to $1\times10^{-4}$ Pa and then, the crucible charged with 2,4-bis[(1,3,3-trimethyl-2-benzoindolinylidene)methyl]-squarylium was energized and film formation was carried out at the deposition rate of 0.2 nm/Sec to give a film thickness of 25 nm. The crucible charged with bis{2-(4-t-butylphenyl)-1,3,4-oxadiazole}-m-phenylene was energized and film formation was carried out at the deposition rate of 0.4 nm/Sec until the film thickness became 50nm. The pressure of the vacuum chamber was raised back to atmospheric pressure and on the resulting device having a structure of supporting substrate/ITO/2,4-bis[(1,3,3-trimethyl- 2-benzoindolinylidene)methyl]-squarylium/bis{2-(4-t-butylphenyl)-1,3,4-oxadiazole}-m-phenylene, a cathode was formed in a similar manner to Example 1. After the EL device was taken out from the deposition chamber, a continuity test was conducted as in Example 1. Consequently, by the application of voltage at 20V, an electric current of 4.1 mA/cm$^2$ flew through the device and red light emission having brightness of 160 cd/M$^2$ was obtained.

EXAMPLE 8

In a similar manner to Example 7 except for the use of 2,4-bis[(1-ethyl-3,3-dimethyl-2-indolinylidene)methyl]-squarylium as an emitter material, an organic EL device was fabricated. The device was subjected to a continuity test as in Example 7. Consequently, by the application of voltage at 20 V, an electric current corresponding to electric density of 5.0 mA/cm$^2$ flew through the device and red light emission having brightness of about 150 cd/m$^2$ was obtained.

EXAMPLES 9 to 12

In each of Examples 9 to 12, an organic EL device was fabricated in a similar manner to Example 1 except for the use of bisstyrylanthracene (BSA) as an emitter host material. The fabrication of the EL device was carried out as in Example 3 so that the weight ratio of the emitter host material to the guest material would be as shown in Table 2. The device was subjected to a continuity test as in Example 3. In addition, the device was subjected to a driving test at the initial brightness of 400 cd/m$^2$ in nitrogen, whereby brightness half-time was judged. As a result, a device excellent in efficiency and driving life can be obtained under the fabrication conditions shown in Table 2.

TABLE 2

|  | weight ratio to BSA (wt. %) | Maximum brightness (cd/m$^2$) | Brightness half-life time (hour) |
| --- | --- | --- | --- |
| Example 9 | 0.001 | 5100 | 2700 |
| Example 10 | 0.1 | 5300 | 2600 |
| Example 11 | 1 | 4500 | 2000 |
| Example 12 | 40 | 1900 | 1300 |

Conventional Example

After a glass substrate having ITO formed thereon, which had been prepared as in Example 1, was attached to a deposition chamber, 1 g of α-NPD was charged as a hole transporting material in a crucible made of high-purity graphite and 1 g of tris(8-quinolinol)aluminum was charged as an emitter material and electron transporting material in another crucible. In a further crucible, 1 g of 4-dicyanomethylene-2-methyl-6-(p-dimethylaminostyryl)-4H-pyran (DCM, doping concentration: 5 wt. %) was charged as a dopant. After the vacuum chamber was evacuated to $1\times10^{-4}$ Pa, the crucible charged with α-NPD was energized and film formation was carried out at deposition rate of 0.3 nm/Sec until the film thickness became 50 nm.

Each crucible charged with tris(8-quinolinol)aluminum and DCM was energized through different deposition power sources to give deposition rates of 0.3 nm/Sec and 0.03 nm/Sec, respectively. When both deposition rates became stable, a shutter was opened. As soon as the thickness of the mixed film reached 30 nm, the deposition pour source for DCM was cut, but deposition of tris(8-quinolinol)aluminum was continued to give a film thickness of 40 nm.

On the device having a structure of supporting substrate/ITO/α-NPD/tris(8-quinolinol)aluminum: DCM/tris(8-quinolinol)aluminum, a cathode was formed in a similar manner to Example 1. After taken out from the deposition chamber, the resulting EL device was subjected to a continuity test as in the above-described example. As a result, when the voltage was applied at 6V, an electric current of 15 mA/cm$^2$ flew through the device and orange-color light emission having the maximum brightness of 12000 cd/m$^2$ was obtained.

Although the maximum brightness was larger than that of the organic EL device of the present invention, the chromaticity was in a orange region as expressed by C.I.E. chromaticity coordinates (X 0.528, Y 0.440) so that with a blue color, the color became white. The color obtained by the combination of three RGB colors was not white but greenish color. Consequently, the device obtained in the conventional example was not suitable for use as a full color display panel device.

What is claimed is:

1. An organic electroluminescent device, which comprises a pair of a cathode and an anode and therebetween, at least one organic thin-film layer containing an emitter layer, wherein said at least one organic thin-film layer comprises a squarylium compound represented by the following structural formula (1):

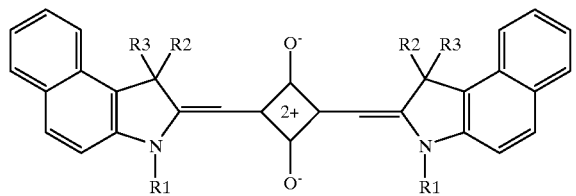

(1)

wherein each of R1 to R3 is independently selected from a group consisting of a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom.

2. An organic electroluminescent device according to claim 1, wherein said emitter layer comprises a green to yellow-light emitting material and a squarylium compound represented by the following structural formula (1):

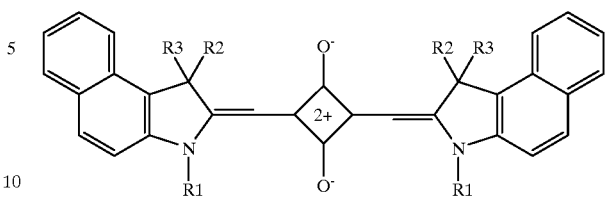

(1)

wherein each of R1 to R3 is independently selected from a group consisting of a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom.

3. An organic electroluminescent device according to claim 1, wherein said emitter layer comprises a quinoline metal complex as a host material and a squarylium compound represented by the following structural formula (1):

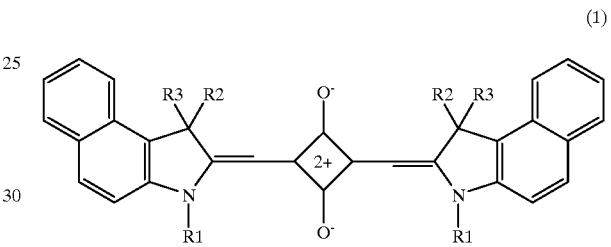

(1)

wherein each of R1 to R3 is independently selected from a group consisting of a hydrogen atom, a hydroxyl group, a substituted or unsubstituted alkyl group having 1 to 5 carbon atoms, a nitro group, a cyano group, a substituted or unsubstituted alkoxy group having 1 to 5 carbon atoms, aryl group or a halogen atom, as a guest material.

4. An organic electroluminescent device according to claim 3, wherein the squarylium compound represented by the structural formula (1) is contained in an amount of 0.001 to 50 wt. % relative to the host material.

* * * * *